United States Patent [19]
Dow et al.

[11] Patent Number: 5,355,800
[45] Date of Patent: * Oct. 18, 1994

[54] COMBINED EED IGNITER MEANS AND MEANS FOR PROTECTING THE EED FROM INADVERTENT EXTRANEOUS ELECTRICITY INDUCED FIRING

[76] Inventors: Robert L. Dow, Rte. 5, Box 415, LaPlata, Md. 20646; Paul W. Proctor, Rte. 2, Kathy La., White Plains, Md. 20695

[*] Notice: The portion of the term of this patent subsequent to Jan. 18, 2011 has been disclaimed.

[21] Appl. No.: 868,249

[22] Filed: Apr. 14, 1992

Related U.S. Application Data

[63] Continuation-in-part of Ser. No. 584,045, Sep. 18, 1990, Pat. No. 5,279,225, which is a continuation-in-part of Ser. No. 479,117, Dec. 13, 1990, Pat. No. 5,036,768.

[51] Int. Cl.$^5$ ............................................. F42B 3/18
[52] U.S. Cl. ................... 102/202.2; 102/202.3; 102/202.8; 102/202.9
[58] Field of Search ............... 102/202.1, 202.2, 202.3, 102/202.4, 202.9, 202.14, 206, 202.8, 202.7

[56] References Cited

U.S. PATENT DOCUMENTS

| | | | |
|---|---|---|---|
| 2,188,020 | 12/1957 | Burklund | 102/202.1 |
| 2,882,820 | 4/1959 | Young | 102/202.14 |
| 3,292,537 | 12/1966 | Gross, Jr. | 102/202.9 |
| 3,572,247 | 3/1971 | Warshall | 102/202.2 |
| 4,708,060 | 11/1987 | Bickes, Jr. et al. | 102/202.7 |
| 4,831,933 | 5/1989 | Nerheim et al. | 102/202.9 |
| 4,924,774 | 5/1990 | Lenzen | 102/202.7 |

FOREIGN PATENT DOCUMENTS 29671 6/1981 European Pat. Off. ......... 102/202.2

Primary Examiner—Stephen M. Johnson
Attorney, Agent, or Firm—Terry M. Gernstein

[57] ABSTRACT

The precision ignition device disclosed in U.S. Pat. No. 4,708,060 is combined with the device disclosed in U.S. Pat. No. 5,036,768, and U.S. Ser. No. 07/584,045 to provide accurate control over the ignition of an EED while also protecting that EED from inadvertent firing caused by exposure to extraneous electricity, such as RF energy or electrostatic energy. The combined device can be connected to a source of power and/or to an external sequential timer for further control over the firing process. A method of fabricating the means for protecting the EED from inadvertent extraneous electricity induced firing is also disclosed.

24 Claims, 4 Drawing Sheets

COMBINED EED IGNITER MEANS AND MEANS FOR PROTECTING THE EED FROM INADVERTENT EXTRANEOUS ELECTRICITY INDUCED FIRING

The present invention is a continuation-in-part of U.S. Ser. No. 07/584,045 filed on Sep. 18, 1990 and now U.S. Pat. No. 5,279,225 (hereinafter referred to as the parent application), which is a continuation-in-part of U.S. Ser. No. 07/479,117, filed on Dec. 13, 1990 and which issued on Aug. 6, 1991 as U.S. Pat. No. 5,036,768 (hereinafter referred to as the grandparent patent). The disclosures of these documents are incorporated herein by reference.

TECHNICAL FIELD OF THE INVENTION

The present invention relates to the general art of electroexplosive devices, and to the particular field of control of the initiation of electroexplosive devices.

BACKGROUND OF THE INVENTION

An electroexplosive device (EED) is an initiator or a system in which an electrical impulse initiates detonation or deflagration of an explosive. As used herein, the term EED is intended to include electric blasting caps (EBC). An EED generally includes a dc power source electrically connected to a firing means via input firing leads. The firing means is of the type which fires an ignition mixture when sufficient current is applied to the firing means. EEDs are used in both the military market and in the civilian market for blasting applications, for ammunition applications as well as for air bags or the like. Because EEDs can rapidly generate large volumes of gas, they also can be used in conjunction with nearly any item which must be rapidly inflated.

The new and varied uses being found for EEDs has generated a concomitant demand for greater precision and accuracy in the operation of such EEDs. As discussed in the 175th Anniversary Edition of the *Blasters' Handbook* published by the Sales Development Section Explosives Products Division of E. I. duPont Nemours & Co in 1977, the disclosure of which is incorporated herein by reference, one primary reason for failures in blasting operations is the inaccuracy associated with the explosives themselves. Precise detonation of explosives can decrease the disadvantages associated with rubble, air blast, vibration, noise, fly rock, and the like. Those skilled in the art realize that the more precise and accurate the control of the explosive detonation, the more precise and accurate the overall blasting operation can be.

For example, if the delay associated with the firing of an EED can be known with extreme precision, the spacing and pattern associated with a particular blasting operation can be set with equal precision. Other advantages of precise control over the detonation of the explosives used in a blasting operation can be understood from the aforementioned *Blasters' Handbook*.

For this reason, the art has included various initiating devices that are intended to provide precise control over the initiation of an explosive. Some of these control devices are discussed in Chapters 7 and 24 of the *Blasters' Handbook*. Further control over the initiation process can be obtained using controlled blasting machines such as manufactured by Research Energy of Ohio, Inc., and discussed in REO Technical Data Bulletin for DC450-50J, CD450A-50J, CD600-100J and CD700-69J. Other sequential blasting machines such as the REO BM175-10ST can be used as can programmable machines such as the REO BM175-10PT machine, or the like.

While these control means have been successful in the past, the increased strictness of the precision requirements placed on the explosive devices both by the blasting applications of EEDs and by the non-blasting applications of EEDs, have resulted in most prior art initiation control means being at a disadvantage.

Therefore, the art has included initiation control means that are capable of extremely accurate and precise control functions. One such control means is the igniter disclosed in U.S. Pat. No. 4,708,060 (the disclosure of which is incorporated herein by reference, and hereinafter referred to as '060). The control means disclosed in this patent includes a non-electrically conducting substrate supporting an electrical material having a negative coefficient of electrical resistivity at an elevated temperature and which defines a pair of spaced apart pads and a connecting bridge having a resistance of less than about three ohms. A major requirement of for this material is that it develop a temperature coefficient of electrical resistivity which is negative at some temperature, e.g., some temperature above room temperature, e.g., about 100° C. The precise temperature is not critical. Essentially all semiconductors will have this property at sufficiently high doping levels. In general, it is preferred that the semiconductor material be doped essentially at or near its saturation level, e.g., approximately $10^{19}$ atoms/cc, e.g. phosphorus atoms for n-type silicon. Lower doping levels may also be operable under appropriate conditions which can be determined routinely in accordance with the guidelines given in this disclosure. For example, doping levels lower by a factor of 2 from this value will also provide adequate properties for the purposes of this invention. Corresponding resistivity values will be in the order of $10^{-3}$ to $10^{-4}$ e.g., about $8 \times 10^{-4}$ $\Omega$cm for the mentioned saturation doping level. However, other than as explained above, resistivity values per se are not critical. An electrical conductor is connected to each metallized layer and explosive material covers the device. When an electrical current passes through the device, the bridge bursts, igniting the explosive material associated with the device. If this patented initiating control device is used, especially if in conjunction with accurate control devices such as the aforementioned REO, Inc device, extremely accurate and precise control of the explosive initiation process can be obtained.

While the patented igniter can be extremely accurate, this device has virtually no means for preventing inadvertent ignition of the associated explosive charge due to extraneous electricity incident on the overall EED. Therefore, use of this patented igniter may tend to increase the risk of inadvertent initiation due to entry of extraneous electricity into the circuit. As discussed in the parent patent application and in the *Blasters' Handbook*, extraneous electricity can be created by stray ground currents, lightning and static electricity from electrical storms, radio frequency sources in the vicinity, induced currents caused by electromagnetic field sources in the vicinity, static electricity generated by wind-transported dust, moving equipment and moving equipment parts, and the like, as well as galvanic currents generated by dissimilar metals touching each other or touching a common conductive material.

The accepted "safe" level of extraneous electricity in EEDs is a function of current required to detonate an EED. If extremely small EEDs are used, as could be the case due to the precise control associated with the abovementioned systems, the safe level of extraneous electricity incident on an EED may be reduced from the 50 milliampres suggested by the Institute of Makers of Explosives (IME).

While the art has included several suggestions for preventing extraneous electricity from inadvertently detonating an EED, many such systems may not be adequate for such small and accurate EEDs as may be possible as a result of the combination of the patented igniter and devices such as the REO, Inc device. For example, prior art means for preventing extraneous electricity from inadvertently activating an EED including safety techniques and procedures, measuring and monitoring devices, and the like, may work well for large EEDs, but may not be adequate for small, precise EEDs.

Tests on the device disclosed in the parent application have shown that device to be extremely effective in preventing passage of current generated by extraneous electricity generated from sources such as RF energy incident on the EED and static electricity to a firing means associated with the EED. For example, tests conducted by the Franklin Institute have found the device disclosed in the parent application to prevent firing electrical current to be generated in the EED firing means even though that EED is subjected to RF energy of as high as 19 watts.

Accordingly, accurate, precise, and perhaps, small EEDs can be protected if they can be combined with the device disclosed in the parent application and the grandparent patent.

OBJECTS OF THE INVENTION

It is a main object of the present invention to provide extremely accurate and precise control of the initiation of an explosive device, such as an EED.

It is another object of the present invention to provide extremely accurate and precise control of the initiation of an explosive device, such as an EED, yet in a manner which is not subject to inadvertent firing due to exposure to extraneous electricity, such as RF energy or electrostatic energy.

It is another object of the present invention to combine the features of the initiation device disclosed in U.S. Pat. No. 4,708,060 with the safety features of the device disclosed in the grandparent patent and in the parent patent application.

It is a specific object of the present invention to use the device disclosed in the parent application with the device disclosed in U.S. Pat. No. 4,708,060 and an external sequential timer.

It is a more specific object of the present invention to combine the device disclosed in U.S. Pat. No. 4,708,060 with an external sequential timer such as manufactured by REO, Inc. and to protect such combined devices from inadvertent firing due to exposure to extraneous electricity using the device disclosed in the parent application.

It is another specific object of the present invention to modify the device disclosed in the parent application to be easily used in conjunction with the device disclosed in U.S. Pat. No. 4,708,060.

SUMMARY OF THE INVENTION

These, and other, objects are achieved by combining the device disclosed in the '060 patent with the device disclosed in the parent application in a manner such that any explosive device using the '060 initiator will be protected from inadvertent activation due to extraneous electricity incident on the EED. In this manner, even extremely high levels of extraneous electricity such as might be associated with near-by lightning or even EMP, may not create sufficient current in the '060 device to fire an associated explosive device.

Combining the protective device from the parent application with the '060 device permits the advantages associated with the '060 device to be realized without the dangers associated with exposure of an EED using that device to extraneous electricity. Furthermore, using these two devices in conjunction with an external sequential timer will permit a firing sequence to be precisely and accurately timed for the maximum effect while minimizing undesired side effects. Great precision and accuracy in any blasting operation can be achieved using the combined device while the disadvantages associated with extraneous electricity can be avoided.

The '060 device D is shown in a general manner in FIG. 1 as including housing H in which an igniter means IM is located. The igniter means includes a ceramic header C having two electrical conductors E extending through the header. The leads are connected to two lands L. The lands are spaced apart to form a bridge B. The lands are mounted on a doped silicon substrate, which is mounted on a sapphire substrate. The sapphire substrate is mounted on the header. An ignition mix I is located to contact the bridge. As discussed above, extraneous electricity, such as RF energy, incident on the device may induce pin-to-case potential PC or pin-to-pin potential PP. Either of these potentials may induce sufficient potential across the bridge B to inadvertently fire the ignition mix.

As was discussed in the parent application, inserting the device disclosed in that parent application between the firing means, in this case the bridge B, and a source of current used to intentionally activate that firing means, prevents current associated with the extraneous electricity from creating sufficient potential across the firing means to activate that firing means.

Therefore, the present invention is embodied in a device that combines the igniter disclosed in the '060 patent with the protection device disclosed in the parent application and in the grandparent patent.

As a further refinement, the present invention combines the just-described combined device with an external sequential control means for even further control of the EED activation.

BRIEF DESCRIPTION OF THE DRAWING FIGURES

FIG. 1 illustrates the device disclosed in U.S. Pat. No. 4,708,060.

DETAILED DESCRIPTION OF THE PREFERRED EMBODIMENT OF THE INVENTION

Figure 2:
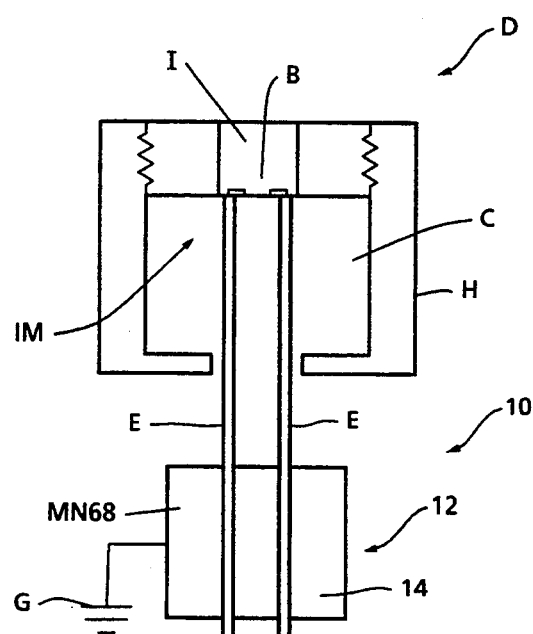
FIG. 2 illustrates the '060 device in combination with the device disclosed in the parent application.

Shown in FIG. 2 is a combined device 10 that includes the device D and device 12 attached to the leads E to make secure electrical and thermal contact therewith. The device 12 is fully disclosed in the parent application and includes a Ferrite element 14 electrically connected to a ground G and in thermal and electrical contact with the leads E. The ground G can include a case associated with the Ferrite element 14. This contact establishes an impedance between the leads and ground that is less than the impedance on the leads between dc power source 16 and the bridge B whereby any pin-to-ground impedance for potential PC is less than the impedance on the leads. As discussed in the parent application, such relative impedances causes RF energy induced current to arc to ground rather than move to the firing means. Electrostatic energy induced potential is simply dissipated to ground due to the connection between the leads and the Ferrite and the Ferrite and ground. Pin-to-pin potential is also simply dissipated in the Ferrite. The DC power source 16 can include an external sequential timer, such as the aforementioned REO, Inc. device.

The combined device 10 shown in FIG. 2, especially in conjunction with a special timer control, will provide extremely precise and accurate control over any EED associated with that combination. Timing delays in the microsecond range can be established and accurately effected. Of course, longer timing delays can be used if suitable. However, the combined device is fully protected against inadvertent firing of the EED due to RF energy or electrostatic energy in the vicinity of the EED.

The combined device 10 shown in FIG. 2 is effective; however, it has certain disadvantages. The FIG. 2 combination may be too limber to be reliable, and may be easily damaged, even if a housing is used to encase the combined device. Any breaks in the joints may also not be apparent until the combination is tested making quality control difficult. Furthermore, varying winding patterns for the device 12 may be difficult due to the limitations placed on such placement by the case H.

Figure 3:
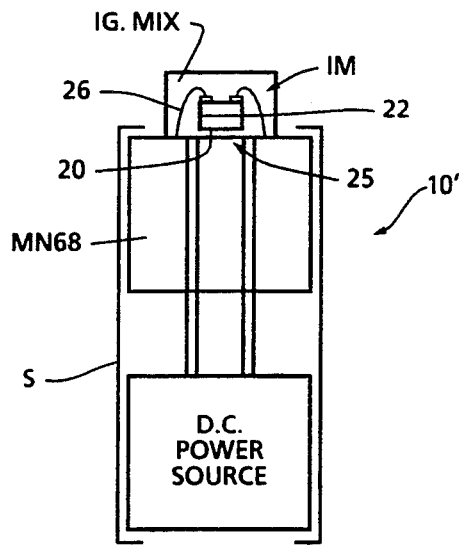
FIG. 3 illustrates a second form of the combination shown in FIG. 2.

Accordingly, device 10' is an alternative form of the device, and is shown in FIG. 3. The device 10' has the igniter means IM mounted on the Ferrite element 14. As discussed above, and in the incorporated '060 patent, the igniter means IM includes a sapphire substrate 20 mounted on the Ferrite element with a doped silicon layer 22 covering the substrate 20. Two lands 24 are spaced apart and define bridge B. Solder 26 electrically connects the leads E to the lands 24. The leads E extend through the ceramic header C. An ignition mix I is located adjacent to the bridge to be fired by that bridge as discussed in the '060 patent. Since the igniter means is mounted directly on the Ferrite element, the overall device 10' is quite stable. An insulation pad 25 may be necessary to prevent heat from the Ferrite element 14 from damaging the igniter means.

The device 10' can be quite reliable since the individual elements thereof can be checked prior to final assembly, and the final assembly can be carried out in a manner that does not vitiate the quality control advantages gained by the use of the two subassemblies 12 and IM. An insulating sleeve S can be used to encase the device 10' if desired.

Figure 1:
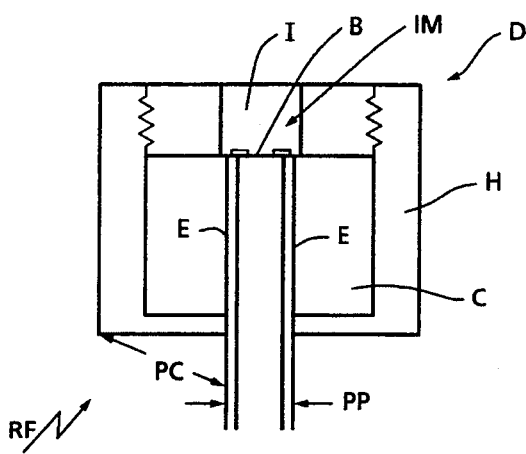
Figure 4:
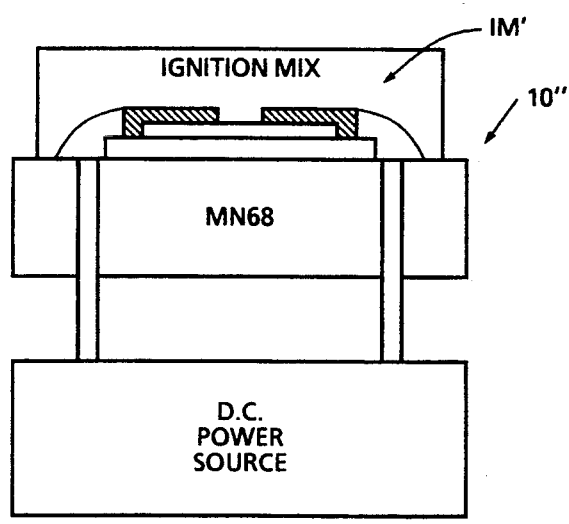
FIG. 4 illustrates a combination between the device disclosed in the parent application and a modified form of the '060 device.
Figure 5:
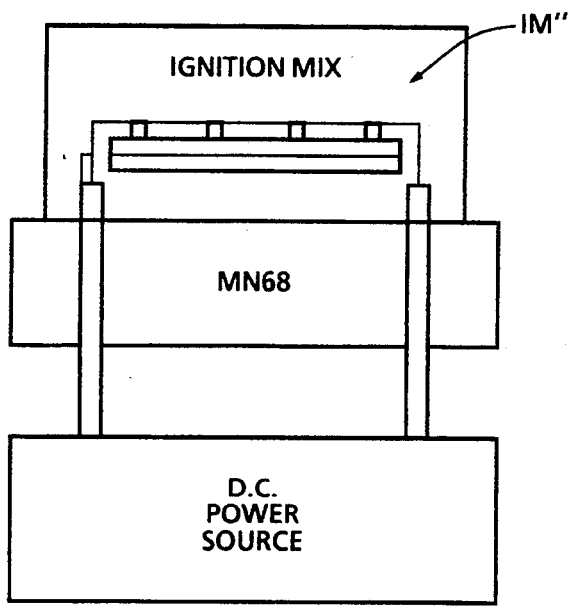
FIG. 5 illustrates a combination between the device disclosed in the parent application and another modified form of the '060 device.

A further alternative form of the device is shown in FIG. 4 as device 10". The device 10" is similar to the device 10', except the igniter means IM' is identical to the igniter means shown in FIG. 1b of the '060 patent in which the lands are formed of aluminum. The device 10''' shown in FIG. 5 is similar to the device 10', except the device 10''' includes an igniter means IM" that is identical to the igniter means shown in FIGS. 3a and 3b of the '060 patent, with the lands being formed by gold lead wire. The device 10''' also has an igniter means IM" that is spaced from the Ferrite element 12.

Figure 6A:
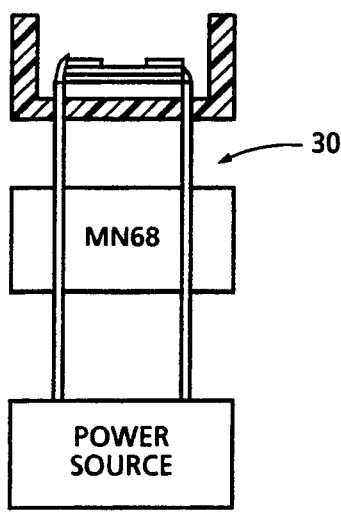
FIG. 6A illustrates another form of the combined device in which a gap is defined between the '060 device and the device disclosed in the parent application.
Figure 6B:
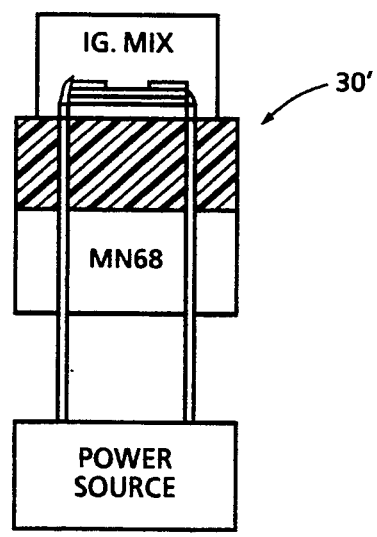
FIG. 6B illustrates another form of the combined device in which a spacer element is located between the '060 device and the device disclosed in the parent application.

The spacing between the igniter means and the Ferrite element accomplishes several functions. First, it facilitates expeditious winding of the Ferrite element by providing space to move the leads. Second, the spacing establishes a proper capacitive gap between the Ferrite element and the igniter means to avoid undesired resonances. This capacitive gap can be set during manufacturing and will be reproducible. The spacing is illustrated in FIGS. 6A and 6B, with the spacing 30 in FIG. 6A being filled by air, and the spacing 30' in FIG. 6B being filled by an insulating material. The igniter means can be any of the above-discussed igniters, and the power source 16 can include a suitable timing means, such as the above-discussed sequential timers.

Figure 7:
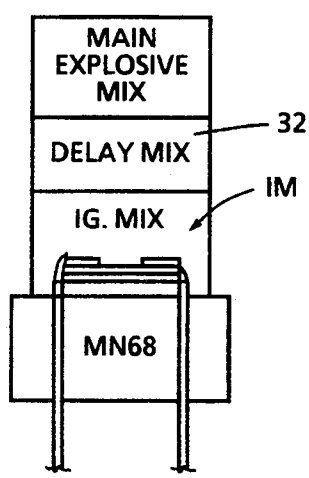
FIG. 7 illustrates the combined device in conjunction with a delay means located adjacent to an ignition mix.

A delay means can be used to further fine tune the firing process. As shown in FIG. 7, a delay mix 32 can be interposed between the ignition mix I and a main explosive charge. The igniter means and the protection element used in conjunction with the delay mix can be any of the above-discussed elements. Suitable gaps can also be established if desired. Electronic timing circuits can also be used to maintain the precision delay tuning required.

Figure 8:
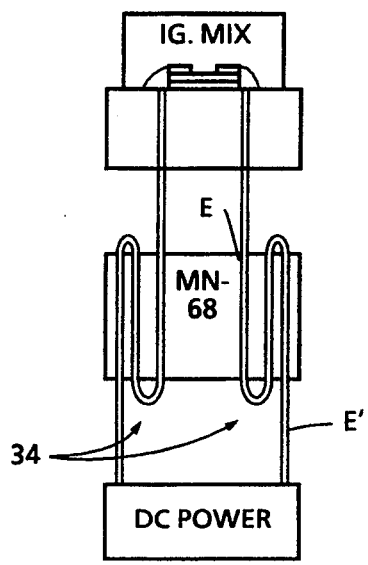
FIG. 8 illustrates a combined device in which the firing lead makes several passes through a Ferrite element.

As discussed in the parent application and the grandparent patent, the firing lead can be wound through the Ferrite device in several manners to provide the most effective protection. One such winding pattern is illustrated in FIG. 8. This winding pattern is similar to the winding pattern disclosed in U.S. Pat. No. 4,378,738, the disclosure of which is incorporated herein by reference. The winding pattern includes a U-shaped section 34 attached to the J-shaped lead E at one end and to the remainder of the lead E' at the other end. The lead E' is then connected to the power source and/or external sequential timer. The other winding patterns disclosed in the U.S. Pat. No. 4,378,738, in the parent application and in the grandparent patent can also be used.

In order to further facilitate fabrication of the overall device, the device of the present invention uses pins for that portion of the firing leads extending through the Ferrite element. These pins are inserted into the Ferrite element during fabrication of that Ferrite element, and the igniter means is then mounted on the pins. The Ferrite element has stakes placed therethrough during the fabrication process, with the stakes being located where the pins are to be placed. The stakes define bores through the Ferrite element, and the pins are placed in the bores. The ends of the pins that extend out of the Ferrite element are trimmed so the pins have the length desired for a particular application. The igniter means is then mounted on the pins.

Figure 9:
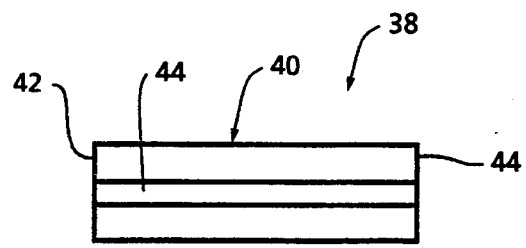
FIG. 9 is a side elevational view of a pin that is used to form electrical and thermal contact between the firing lead and the Ferrite element in a manner that accommodates thermal expansion and contraction without endangering the Ferrite element while establishing a snug fit.
Figure 10:
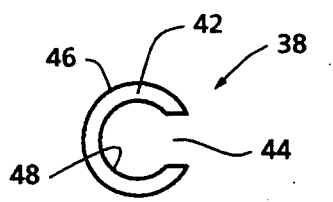
FIG. 10 is a top plan view of the pin shown in FIG. 9.
Figure 11:
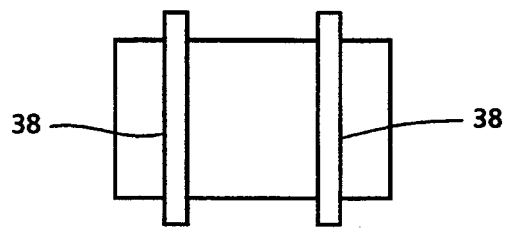
FIG. 11 is a side elevational view showing a Ferrite element having pins inserted therethrough.

The preferred form of a pin 38 is shown in FIGS. 9 and 10, and includes a C-shaped body 40. The body 40 includes two ends 42 and 44, and has a slot 44 extending from one end to the other for the entire length of the body. The body is hollow, and is formed of resilient, corrosion-resistant, electrically and thermally conductive material, such as aluminum or the like. The pin has an outer surface 46 and an inner surface 48, with an outer diameter being associated with the outer surface 46. The bores defined in the Ferrite element have an inner diameter that is slightly less than the outer diameter of the pins whereby the pins must be compressed to fit into the bores. Such compression causes the pins to expand against the Ferrite when released and to be biased against the Ferrite with sufficient force to establish the desired electrical and thermal contact between the pins and the Ferrite as discussed in the parent application. The pins must also be fit into the Ferrite element in a manner such that temperature cycling of the Ferrite element will not either loosen the pin sufficiently to permit the pin to fall out of the Ferrite element upon expansion of the Ferrite, or cause the pin to damage the Ferrite upon contraction of the Ferrite. The pins are shown in place in FIG. 11. The preferred form of the pins is disclosed in Military Standard MS 171401 thru 171900 as approved on May 15, 1953 and on Nov. 3, 1980. These pins can also include chamfered ends if so desired. However, other forms of pins and biasing means can be used without departing from the scope of the present disclosure.

Figure 12:
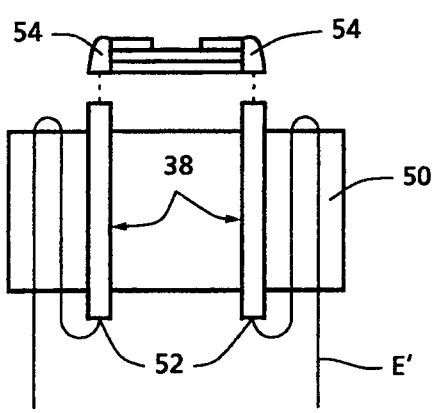
FIG. 12 is an exploded side elevational view showing the Ferrite element with pins therein and a firing lead passing through the Ferrite element.
Figure 13:
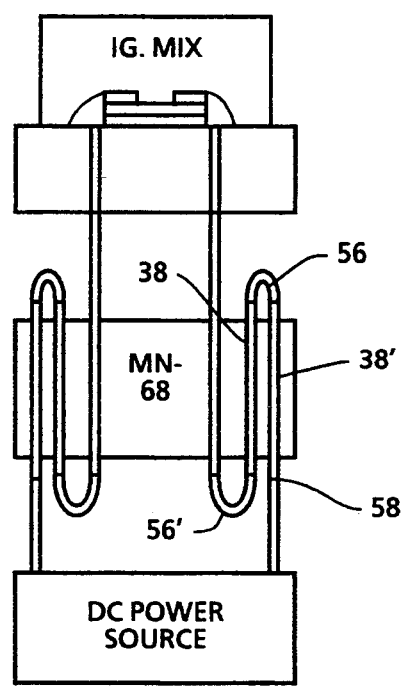
FIG. 13 is a side elevational view showing several pins in a Ferrite element.

The pins can be placed by hand or using automated machines that are commonly used to place spring pins into other elements. The igniter means can then be mounted on the pins as indicated in FIGS. 12 and 13 by welding or the like. As shown in FIG. 12, a winding pattern can be established in the Ferrite element. The winding pattern shown in FIG. 12 uses wires 50 to form the U-shaped winding pattern. The wires can simply be pressed into the Ferrite and soldered to the pins as indicated at solder joint 52. The wires then form the leads E' that are connected to the power source or to an external sequential timer. Solder joints 54 are used to connect the igniter means to the pins. As indicated in FIG. 13, further pins 38' can be used in place of the U-shaped wire sections, with electrical connectors 56 and 56' being soldered to the pins to electrically connect pins 38 and 38'. The leads E' are then connected, as by solder joints 58, to the pins 38'. Multiple bores and pin and wire combinations can be defined in the Ferrite in any suitable pattern to accommodate the pins in a manner that establishes any desired "winding" pattern.

Figure 14:
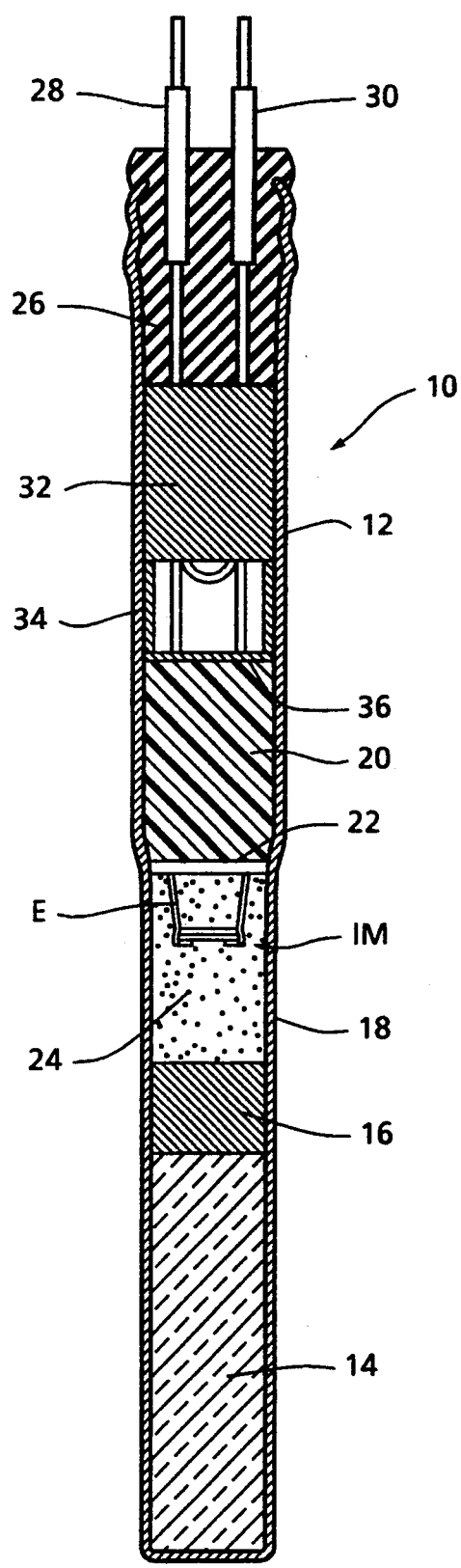
FIG. 14 is a cut away elevational view of an EED disclosed in the grandparent patent in which the combined device is used.
Figure 15:
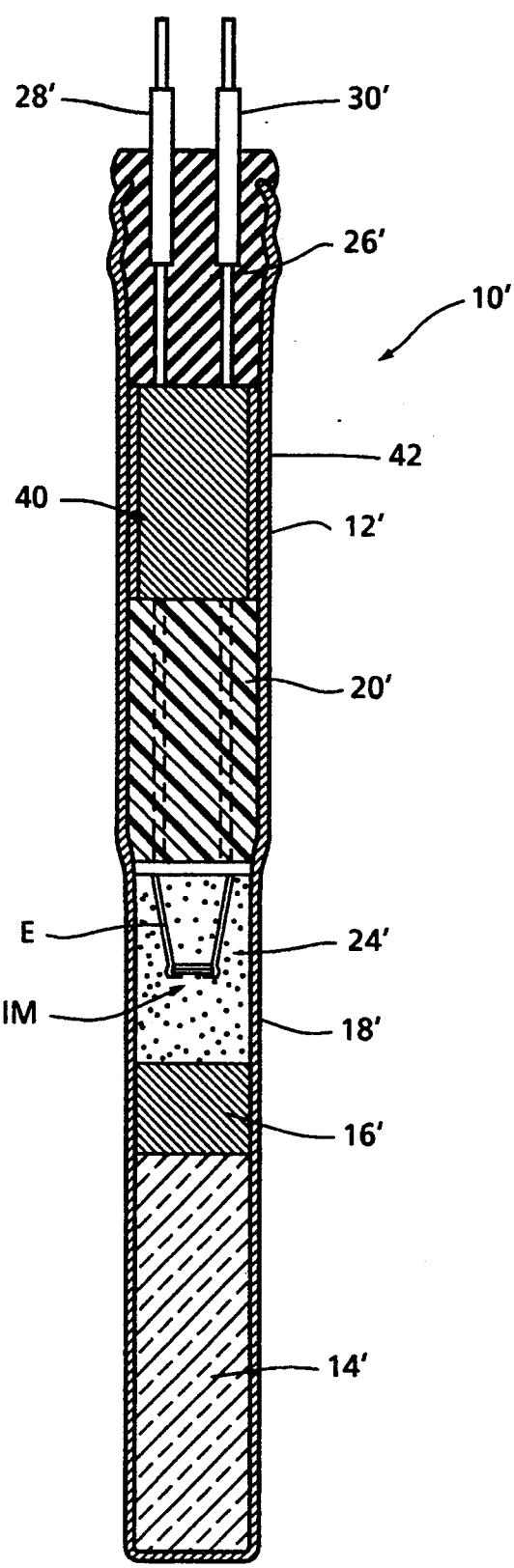
FIG. 15 is a cut away elevational view of anther EED as disclosed in the grandparent patent in which the combined device is used.

The device 10 can be used in an EED such as disclosed in the grandparent patent. Two forms of such EED are shown in FIGS. 14 and 15, with these figures corresponding to FIGS. 1 and 2 of the grandparent patent. A complete discussion of the EEDs shown in FIGS. 14 and 15 is presented in the grandparent patent. The igniter means are shown in FIGS. 14 and 15 as being placed on the firing leads in place of the bridgewire disclosed in that patent. Otherwise, the EEDs shown in FIGS. 14 and 15 are identical to the EEDs disclosed in that patent.

It is understood that while certain forms of the present invention have been illustrated and described herein, it is not to be limited to the specific forms or arrangements of parts described and shown. For example, baluns can be used in place of the choke disclosed herein. Multiple winding patterns can also be used if necessary

We claim:

1. In combination:
   A) an explosive device that includes
      a non electrically conducting substrate,
      an electrical material mounted on said substrate and having a negative temperature coefficient of electrical resistivity at an elevated temperature, said electrical material covering an area of said substrate and defining two spaced pads connected by a bridge, each of said pads having an area, said bridge having an area and forming a plasma when electrical current is passed therethrough, and the area of each of said pads being much larger than the area of said bridge, said bridge having an electrical resistance of less than about three ohms,
      a metallized layer covering each of said spaced pads,
      an electrical conductor connected to each of said metallized layers, with electrical resistance between said electrical conductors being substantially determined by the electrical resistance of said bridge, and
      an explosive material covering said metallized layer, the area of said bridge in contact with said explosive material being sufficient to ignite said explosive material when said bridge forms said plasma due to said electrical current passing therethrough;
   B) a dc power source connected to said electrical conductors; and
   C) means for protecting said explosive device from inadvertent extraneous electricity induced firing, said means including
      a ground element electrically separated from said electrical conductors by a first impedance, an impedance in said electrical conductors between said dc power source and said explosive device which is greater than said first impedance when exposed to extraneous electricity.

2. The combination defined in claim 1 wherein said explosive device is an EED.

3. The combination defined in claim 1 wherein said explosive device is an EBC.

4. The combination defined in claim 1 wherein said impedance includes a Ferrite element.

5. The combination defined in claim 4 wherein at least one of said electrical conductors includes a pin in said Ferrite element, and means biasing said pin into electrical and thermal contact with said Ferrite element.

6. The combination defined in claim 5 wherein said pin is selected from Military Specification MS 171401–171900.

7. The combination defined in claim 5 further including additional electrical conductors in said Ferrite.

8. The combination defined in claim 7 wherein said electrical conductors are U-shaped.

9. The combination defined in claim 5 wherein said pin is formed of corrosion-resistant material.

10. The combination defined in claim 1 wherein said extraneous electricity includes RF energy.

11. The combination defined in claim 1 wherein said extraneous electricity includes static electricity.

12. The combination defined in claim 1 further including an external sequential timer means connected to the electrical conductors.

13. The combination defined in claim 1 further including a delay mixture adjacent to said explosive material.

14. The combination defined in claim 1 wherein said means for protecting said explosive device from inadvertent extraneous electricity induced firing is spaced from said explosive device.

15. The combination defined in claim 14 further including a spacing means located between said means for protecting said explosive device from inadvertent extraneous electricity induced firing and said explosive device.

16. The device defined in claim 1 wherein said explosive material is spaced from said means for protecting said explosive device from inadvertent extraneous electricity induced firing.

17. The device defined in claim 1 wherein said explosive material is mounted on said means for protecting said explosive device from inadvertent extraneous electricity induced firing.

18. A device for preventing inadvertent firing of an EED due to exposure to extraneous electricity including
A) an input lead for connecting a firing means to a dc power source to pass firing current through said firing means;
B) a ground element electrically separated from said input lead by a first impedance; and
C) an impedance in said input lead between said dc power source and said firing means which is greater than said first impedance when exposed to said extraneous electrical energy, said impedance including a Ferrite element having at least two bores defined therethrough, an electrically conductive pin in each said bore, and means biasing said electrically conductive pin into electrical and thermal contact with said Ferrite element.

19. The device defined in claim 18 wherein said pin is selected from Military Specification MS 171401–171900.

20. A device for preventing inadvertent firing of an EED due to exposure to extraneous electricity including
A) an input lead for connecting a firing means to a dc power source to pass firing current through said firing means;
B) a ground element electrically separated from said input lead by a first impedance; and
C) an impedance in said input lead between said dc power source and said firing means which is greater than said first impedance when exposed to said extraneous electrical energy, said impedance including a Ferrite element having at least one conductive path defined therethrough and connected to said input lead.

21. The device defined in claim 20 wherein said conductive path includes a pin biased into contact with said Ferrite element.

22. The device defined in claim 21 wherein said pin is biased against said Ferrite element to establish thermal and electrical contact with said Ferrite element.

23. A device for preventing inadvertent firing of an EED due to exposure to EMP including
A) an input lead for connecting a firing means to a dc power source to pass firing current through said firing means;
B) a ground element electrically separated from said input lead by a first impedance; and
C) an impedance in said input lead between said dc power source and said firing means which is greater than said first impedance when exposed to extraneous electrical energy, said impedance including a Ferrite element having at least two bores defined therethrough, an electrically conductive pin in each said bore, and means biasing said electrically conductive pin into electrical and thermal contact with said Ferrite element.

24. A device for preventing inadvertent firing of an EED due to exposure to nearby lightning strikes including
A) an input lead for connecting a firing means to a dc power source to pass firing current through said firing means;
B) a ground element electrically separated from said input lead by a first impedance; and
C) an impedance in said input lead between said dc power source and said firing means which is greater than said first impedance when exposed to extraneous electrical energy, said impedance including a Ferrite element having at least two bores defined therethrough, an electrically conductive pin in each said bore, and means biasing said electrically conductive pin into electrical and thermal contact with said Ferrite element.

* * * * *